(12) United States Patent
Spiekermann et al.

(10) Patent No.: US 11,643,690 B2
(45) Date of Patent: May 9, 2023

(54) EARLY DETECTION OF PRELIMINARY STAGES OF TESTICULAR GERM CELL TUMORS

(71) Applicant: miRdetect GmbH, Breman (DE)

(72) Inventors: Meike Spiekermann, Bremen (DE); Nina Winter, Hambergen (DE); Gazanfer Belge, Bremen (DE); Arlo Radtke, Bremen (DE)

(73) Assignee: miRdetect GmbH, Bremen (DE)

( * ) Notice: Subject to any disclaimer, the term of this patent is extended or adjusted under 35 U.S.C. 154(b) by 369 days.

(21) Appl. No.: 16/341,383

(22) PCT Filed: Nov. 2, 2017

(86) PCT No.: PCT/EP2017/078079
§ 371 (c)(1),
(2) Date: Apr. 11, 2019

(87) PCT Pub. No.: WO2018/083186
PCT Pub. Date: May 11, 2018

(65) Prior Publication Data
US 2020/0056243 A1    Feb. 20, 2020

(30) Foreign Application Priority Data
Nov. 2, 2016    (EP) .................................... 16196813

(51) Int. Cl.
*C12Q 1/6886*    (2018.01)
(52) U.S. Cl.
CPC ..... *C12Q 1/6886* (2013.01); *C12Q 2600/178* (2013.01)
(58) Field of Classification Search
CPC ............... C12Q 1/6851; C12Q 1/6886; C12Q 2600/178
See application file for complete search history.

(56) References Cited

U.S. PATENT DOCUMENTS

2018/0163264 A1    6/2018    Spiekermann et al.

FOREIGN PATENT DOCUMENTS

CN    101363057    2/2009

OTHER PUBLICATIONS

Radtke, A et al., Can germ cell neoplasia in situ be diagnosed by measuring serum levels of microRNA371a-3p? J. Cancer Res. Clin. Oncol., vol. 143, pp. 2383-2392 (Year: 2017).*
Montironi, R., Intratubular Germ Cell Neoplasia of the Testis: Testicular Intraepithelial neoplasia, Europ. Urology, vol. 41, pp. 651-654 (Year: 2002).*
International Search Report and Written Opinion, PCT/EP2017/078079, dated Feb. 8, 2018, 11 pages.
International Preliminary Report on Patentability, PCT/EP2017/078079, dated May 16, 2019, 8 pages.
Dieckmann et al., "MicroRNA miR-371a-3p—A novel serum biomarker of testicular germ cell tumors: Evidence for specificity from measurements in testicular vein blood and in neoplastic hydrocele fluid," Urologia Internationalis, pp. 1-8, Mar. 19, 2016.
Novotny et al., "MicroRNA expression profiling of carcinoma in situ cells of the testis," Endocrine-Related Cancer 19(3):365-379, May 24, 2012.
Pelloni et al., "Differential expression of miRNAs in the seminal plasma and serum of testicular cancer patients," Endocrine 57(3):518-527, Oct. 28, 2016.
Spiekermann et al., "MicroRNA miR-371a-3p in serum of patents with germ cell tumors: Evaluations for establishing a serum biomarker," Andrology 3(1):78-84, Sep. 4, 2014.
Van Agthoven et al., "Accurate primary germ cell cancer diagnosis using serum based microRNA detection (ampTSmiR test)," Oncotarget 8(35):58037-58049, Jul. 27, 2016.
Anandaram (Nov. 2017) "Computational Analysis of Expression Based Regulation in Psoriasis: An Approach of Systems Biology to Understand Disease Pathology and Predict Potential Regulators," J. Sys. Biol. Res. 1(1): 1-17.
Chen et al. (2009) "Reproducibility of quantitative RT-PCR array in miRNA expression profiling and comparison with microarray analysis," BMC Genomics 10(407): 1-10.
Exiqon (2013) "Data Analysis Guide for the miRCURY LNA Universal RT microRNA Ready-to-Use PCR panels using Exiqon GenEx software version 2.5," pp. 1-53.
"Human miRNome miScript miRNA PCR Array," (2013) Qiagen Product Sheet, pp. 1-21.
International Search Report & Written Opinion, International Application No. PCT/EP2016/059604, dated Jul. 19, 2016, 14 pages.
Korenkova et al. (2015) "Pre-amplification in the context of high-throughput qPCR gene expression experiment," BMC Molecular Biology 16(5):1-10.
Mengual et al. (2008) "Multiplex preamplification of specific cDNA targets prior to gene expression analysis by TaqMan Arrays," BMC Research Notes 1(21):1-8.
Murray et al. (publicly available Dec. 2015) "A pipeline to quantify serum and cerebrospinal fluid microRNAs for diagnosis and detection of relapse in paediatric malignant germ-cell tumours," British Journal of Cancer (Jan. 2016) 114:151-162.
Qiagen, miScript miRNA PCR Array Handbook, May 2012, 60 pages.
Qiagen, "miScript PreAmp Handbook," Aug. 2012, 52 pages.
Semmelmann et al. (2013) "miRNA biomarker discovery— overcoming limiting sample material," Qiagen Scientific Article, pp. 1-12.
Notification of First Office Action dated Oct. 9, 2022 in corresponding Chinese Patent Application No. 201780067302.2.

(Continued)

*Primary Examiner* — Teresa E Strzelecka
(74) *Attorney, Agent, or Firm* — Leydig, Voit & Mayer, Ltd.

(57) ABSTRACT

The present invention relates to methods of detecting preliminary stages of testicular germ cell tumors, more particularly testicular intraepithelial neoplasia (TIN), in a subject and to the use of miR-371a-3p as a biomarker for the detection of TIN. It further relates to the use of miR-371a-3p-specific primers and/or miR-371a-3p-specific probes and of corresponding kits for the detection of TIN.

12 Claims, 3 Drawing Sheets
Specification includes a Sequence Listing.

(56) References Cited

OTHER PUBLICATIONS

Tanriverdi et al. (2016) "Comparison of RNA isolation and associated methods for extracellular RNA detection by high-throughput quantitative polymerase chain reaction" *Analytical Biochemistry* 501: 66-74.

* cited by examiner

EARLY DETECTION OF PRELIMINARY STAGES OF TESTICULAR GERM CELL TUMORS

CROSS-REFERENCE TO RELATED APPLICATIONS

This application is a U.S. National Stage Application under 35 U.S.C. § 371 of International Application No. PCT/EP2017/078079, filed Nov. 2, 2017, which claims the benefit of and priority to European Patent Application No. 16196813.6, filed Nov. 2, 2016. Each of these applications is hereby incorporated by reference in its entirety.

REFERENCE TO A SEQUENCE LISTING

A sequence listing containing SEQ ID NO: 1 is provided herewith in a computer-readable nucleotide/amino acid .txt file and is specifically incorporated by reference.

TECHNICAL FIELD OF THE INVENTION

The present invention relates to methods of detecting preliminary stages of testicular germ cell tumors, more particularly testicular intraepithelial neoplasia (TIN), in a subject and to the use of miR-371a-3p as a biomarker for the detection of TIN. It further relates to the use of miR-371a-3p-specific primers and/or miR-371a-3p-specific probes and of corresponding kits for the detection of TIN.

BACKGROUND OF THE INVENTION

Testicular germ cell cancer is the most frequently occurring cancer in young men aged between 20 and 45. With early detection, appropriate treatment and close monitoring, the chances of recovery from testicular cancer are very good, although the long-term effects of treatment and monitoring are immense, and the risk of re-developing testicular cancer or suffering a relapse may be up to 31% depending on the tumor type and stage. The known risk factors for the development of testicular cancer include family history and undescended testicles (cryptorchidism), which increases the risk of developing testicular cancer four-fold.

Testicular germ cell cancer arises from the precursor lesion "germ cell neoplasia in situ (GCNIS)", also referred to as "carcinoma in situ (CIS)", "intratubular germ cell neoplasia, unclassified (IGCNU)" and "testicular intraepithelial neoplasia (TIN)" (Berney D. M. et al., 2016, Histopathology 69(1):7-10; Moch H. et al., 2016, Eur Urol 70(1):93-105). TIN is the uniform precursor of testicular germ cell tumors and it may be present in a testicle years before testicular germ cell cancer becomes invasive (Dieckmann K. P. & Skakkebaek N. E., 1999, Int J Cancer 83(6):815-22). 50% of the testes bearing the precursor will progress to invasive cancer within 5 years and 70% will do so within 7 years. Practically, almost all of the testicles bearing TIN will finally develop cancer (Skakkebaek N. E. et al., 1987, Int J Androl 10(1):19-28).

Therefore, an earlier detection of TIN and appropriate subsequent treatment could protect patients from the development of invasive testicular germ cell cancer.

Up until now, surgery is the only possibility to detect TIN in the testicular tissues of a patient. As surgery will not be performed without a serious suspicion, the detection of TIN is, therefore, rather random. Thus, there is a need for a non-invasive, e.g., blood serum-based, method for the detection of TIN.

miRNAs of the miR-371-3 cluster were original detected in germ cell tumor (GCT) tissue (Palmer R. D. et al., 2010, Cancer Res 70(7):2911-23), and independent studies confirmed elevated serum levels (Dieckmann K. P. et al., 2012, Br J Cancer 107(10):1754-60; Gillis A. J. et al., 2013, Mol Oncol 7(6):1083-92). However, previous attempts to establish a link between (serum) expression levels of miRNAs of the miR-371-3 cluster and TIN have failed (Spiekermann M. et al., 2014, Andrology 3(1):78-84; van Agthoven T. & Looijenga L. H., 2016, Oncotarget DOI:10.18632/oncotarget.10867).

By using particular methods of detection (first described in PCT/EP2016/059604), the present inventors have now shown, for the first time, that body fluid expression levels of the specific miRNA miR-371a-3p can serve as a biomarker for the presence of TIN, distinguishing TIN patients from healthy individuals.

SUMMARY OF THE INVENTION

In one aspect, the present invention relates to a method of detecting testicular intraepithelial neoplasia (TIN) in a subject, the method comprising determining the expression level of miR-371a-3p in a biological sample from the subject, wherein the expression level of miR-371a-3p is indicative of the presence or absence of TIN in the subject.

In one embodiment, the method comprises the steps of:
(i) providing a batch A comprising cDNA isolated/obtained from the biological sample, wherein step (i) comprises the steps of:
  (ia) isolating RNA from the biological sample; and
  (ib) converting the RNA isolated in step (ia) into cDNA, thereby providing batch A comprising the cDNA;
(ii) providing three or more aliquots of batch A provided in step (i) and performing an independent polymerase chain reaction (PCR) with each of the three or more aliquots in order to amplify miR-371a-3p, thereby providing three or more batches B comprising the amplified miR-371a-3p; and
(iii) mixing equal amounts of the three or more batches B, thereby providing a batch C, and determining the level of miR-371a-3p in batch C by a PCR-based approach, wherein the level determined in step (iii) corresponds to the expression level of miR-371a-3p in the biological sample.

In another embodiment, the method comprises the steps of:
(i) providing a batch A comprising cDNA isolated/obtained from the biological sample, wherein step (i) comprises the steps of:
  (ia) isolating RNA from the biological sample; and
  (ib) converting the RNA isolated in step (ia) into cDNA, thereby providing batch A comprising the cDNA;
(ii) providing three or more aliquots of batch A provided in step (i) and performing an independent polymerase chain reaction (PCR) with each of the three or more aliquots in order to amplify miR-371a-3p, thereby providing three or more batches B comprising the amplified miR-371a-3p; and
(iii) determining the level of miR-371a-3p in each of the three or more batches B by a PCR-based approach and calculating the mean value of the three or more levels of miR-371a-3p determined by the PCR-based approach, wherein the mean value calculated in step (iii) corresponds to the expression level of miR-371a-3p in the biological sample.

In one embodiment, an expression level of miR-371a-3p, which is increased as compared to a control, is indicative of the presence of TIN in the subject.

In one embodiment, an expression level of miR-371a-3p, which is higher than a predefined cut-off value, is indicative of the presence of TIN in the subject.

In one embodiment, the biological sample is selected from the group consisting of body fluid, tissue, cells, cell lysate and cell culture supernatant.

In one embodiment, the body fluid is selected from the group consisting of blood serum, blood plasma, seminal plasma, hydrocele fluid, spermatocele fluid, whole blood, urine, amniotic fluid, exudate, sputum, saliva and cerebrospinal fluid.

In one embodiment, the body fluid is blood serum.

In one embodiment, the tissue is selected from the group consisting of native tissue, snap-frozen tissue and formalin-fixed and paraffin-embedded (FFPE) tissue.

In one embodiment, three aliquots of batch A are provided in step (ii).

In one embodiment, the PCR-based approach is quantitative real-time PCR (qRT-PCR) or digital PCR (dPCR).

In another aspect, the present invention relates to the use of miR-371a-3p as a biomarker for the detection of testicular intraepithelial neoplasia (TIN).

In one embodiment, miR-371a-3p is used as a body fluid-based biomarker, wherein, preferably, the body fluid is as defined above.

In one embodiment, miR-371a-3p is used as a blood-based biomarker, in particular a blood serum-based biomarker.

In another aspect, the present invention relates to the use of at least one miR-371a-3p-specific primer and/or a miR-371a-3p-specific probe for the detection of testicular intraepithelial neoplasia (TIN).

In another aspect, the present invention relates to at least one miR-371a-3p-specific primer and/or a miR-371a-3p-specific probe for use in a method of detecting testicular intraepithelial neoplasia (TIN), wherein, preferably, the method is as defined above.

In another aspect, the present invention relates to the use of a kit comprising at least one miR-371a-3p-specific primer and/or a miR-371a-3p-specific probe for the detection of testicular intraepithelial neoplasia (TIN).

In one embodiment, the kit further comprises means for isolating RNA from a biological sample and/or means for converting the RNA isolated from the biological sample into cDNA.

In one embodiment, the biological sample is a body fluid as defined above. In one embodiment, the body fluid is blood serum.

In another aspect, the present invention relates to a kit as defined above for use in a method of detecting testicular intraepithelial neoplasia (TIN), wherein, preferably, the method is as defined above.

In yet another aspect, the present invention relates to a method of treating testicular intraepithelial neoplasia (TIN) in a subject or of preventing testicular cancer, more particularly testicular germ cell cancer, in a subject, the method comprising (i) detecting TIN in the subject by a method as defined above and (ii) providing therapy to the subject, wherein, preferably, the therapy is radiotherapy, orchiectomy and/or chemotherapy.

DETAILED DESCRIPTION OF THE INVENTION

Figure 1:
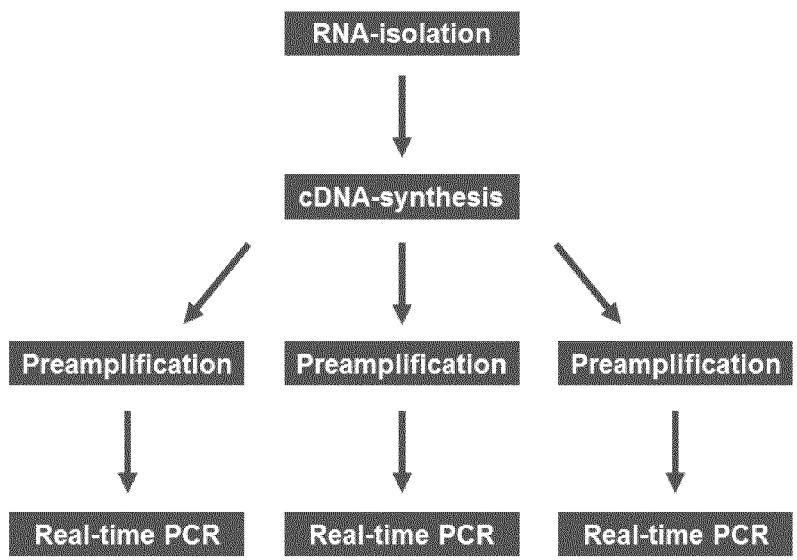
FIG. 1 shows a schematic representation of a method in accordance with the present invention (Example 1). Subsequent to three qRT-PCRs, the arithmetic mean value is calculated for the evaluation of the data.

Although the present invention is described in detail above and below, it is to be understood that this invention is not limited to the particular methodologies, protocols and reagents described herein as these may vary. It is also to be understood that the terminology used herein is for the purpose of describing particular embodiments only, and is not intended to limit the scope of the present invention, which will be limited only by the appended claims. Unless defined otherwise, all technical and scientific terms used herein have the same meanings as commonly understood by one of ordinary skill in the art.

In the following, certain elements of the present invention will be described. These elements may be listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments, which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., Molecular Cloning: A Laboratory Manual, $3^{rd}$ Edition, J. Sambrook et al. eds., Cold Spring Harbor Laboratory Press, Cold Spring Harbor 2000).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Testicular intraepithelial neoplasia (TIN) is a precursor lesion for testicular germ cell tumors and is also known as "germ cell neoplasia in situ (GCNIS)", "carcinoma in situ (CIS)" or "intratubular germ cell neoplasia, unclassified (IGCNU)". These terms are used interchangeably in the context of the present invention. The terms "testicular germ cell tumor" and "testicular germ cell cancer", as used interchangeably herein, refer to testicular tumors/cancers derived from germ cells in the testicles (about 95% of all testicular cancers).

microRNAs (miRNAs) are short, highly conserved, non-coding RNAs, which play an important role in the complex network of gene regulation. They specifically bind to messenger RNAs (mRNAs) and control gene expression through regulation of mRNA stability and translation. Generally, miRNAs consist of 21 to 23 nucleotides. In one embodiment, miR-371a-3p, as referred to herein, is human miR-371a-3p (*Homo sapiens*, hsa). In one embodiment, hsa-miR-371a-3p has the (5'-3') sequence AAGUGCCGCCAUCUUUUGAGUGU (SEQ ID NO: 1).

The term "expression level", as used herein, may refer to the relative expression level, i.e., the expression level of miR-371a-3p relative to the expression level(s) of one or more reference nucleic acid molecules (e.g., another miRNA, such as miR-93-5p), or to the absolute expression level, i.e., the actual amount of miR-371a-3p. In accordance with the present invention, "determining the expression level of miR-371a-3p in a biological sample" may be "determining the presence or absence of miR-371a-3p in a biological sample". According to the present invention, the expression level (or the presence or absence) of miR-371a-3p in the biological sample is indicative of the presence, absence and/or extent/progression of TIN in a subject from which the biological sample is obtained. In one embodiment, an expression level of miR-371a-3p, which is increased as compared to a control (e.g., the expression level of miR-371a-3p in a subject not having TIN), is indicative of the presence of TIN in the subject. In one embodiment, an expression level of miR-371a-3p, which is higher than a predefined cut-off value, is indicative of the presence of TIN in the subject. In one embodiment, the relative quantity (RQ) of miR-371a-3p is determined, wherein, preferably, the cut-off value is 5.

The term "nucleic acid molecule", as used herein, may be DNA or RNA.

In the context of the present invention, the term "DNA" relates to a molecule, which comprises deoxyribonucleotide residues and is preferably entirely or substantially composed of deoxyribonucleotide residues. "Deoxyribonucleotide" relates to a nucleotide, which lacks a hydroxyl group at the 2'-position of a β-D-ribofuranosyl group. The term "complementary DNA (cDNA)", as used herein, refers to double-stranded DNA synthesized from an RNA template in a reaction catalyzed by the enzyme reverse transcriptase.

In the context of the present invention, the term "RNA" relates to a molecule, which comprises ribonucleotide residues and is preferably entirely or substantially composed of ribonucleotide residues. "Ribonucleotide" relates to a nucleotide with a hydroxyl group at the 2'-position of a β-D-ribofuranosyl group.

The methods described herein and used in accordance with the presence invention (see also PCT/EP2016/059604) allow the detection of specific nucleic acid molecules, e.g., miR-371a-3p, at the lower detection limit. In one embodiment, the term "lower detection limit" refers to the lower detection limit provided by a PCR-based approach, such as quantitative real-time PCR (qRT-PCR) or digital PCR (dPCR).

In one embodiment, the term "lower detection limit" means that the concentration of the specific nucleic acid molecule, e.g., miR-371a-3p, in the biological sample is $\leq 1\times 10^{-11}$ M, or $\leq 1\times 10^{-12}$ M, or $\leq 1\times 10^{-13}$ M, or $\leq 1\times 10^{-14}$ M, or $\leq 1\times 10^{-15}$ M, or $\leq 1\times 10^{-16}$ M. In one embodiment, the term "lower detection limit" means that the concentration of the specific nucleic acid molecule, e.g., miR-371a-3p, in the biological sample is between $1\times 10^{-11}$ M and $1\times 10^{-17}$ M, or $1\times 10^{-12}$ M and $1\times 10^{-17}$ M, or $1\times 10^{-13}$ M and $1\times 10^{-17}$ M, or $1\times 10^{-14}$ and $1\times 10^{-17}$ M, or $1\times 10^{-15}$ and $1\times 10^{-17}$ M, or $1\times 10^{-16}$ and $1\times 10^{-17}$ M.

In one embodiment, the term "lower detection limit" means that the number of the specific nucleic acid molecules, e.g. miR-371a-3p molecules, in the biological sample is $\leq 10000$, or $\leq 5000$, or $\leq 2500$, or $\leq 1000$, or $\leq 500$, or $\leq 250$. In one embodiment, the term "lower detection limit" means that the number of the specific nucleic acid molecules in the biological sample is between 20 and 10000, or 20 and 5000, or 20 and 2500, or 20 and 1000, or 20 and 500, or 20 and 250. In one embodiment, the term "lower detection limit" means that the number of the specific nucleic acid molecules in the biological sample is between 50 and 10000, or 50 and 5000, or 50 and 2500, or 50 and 1000, or 50 and 500, or 50 and 250. In one embodiment, the term "lower detection limit" means that the number of the specific nucleic acid molecules in the biological sample is between 100 and 10000, or 100 and 5000, or 100 and 2500, or 100 and 1000, or 100 and 500, or 100 and 250.

In one embodiment, the concentrations or numbers of the specific nucleic acid molecule(s) recited herein refer to the concentrations or numbers of the specific nucleic acid molecule(s) in batch A comprising cDNA isolated/obtained from the biological sample (wherein a specific RNA molecule is converted into the corresponding cDNA molecule). In one embodiment, the concentrations or numbers of the specific nucleic acid molecule(s) recited herein refer to the concentrations or numbers of the specific nucleic acid molecule(s) in the RNA isolated/extracted from the biological sample.

In one embodiment, the independent PCR performed with each of the three or more aliquots in step (ii) of the methods according to the present invention is a preamplification PCR reaction.

Preferred biological samples in accordance with the present invention are selected from the group consisting of body fluid, tissue, cells, cell lysate and cell culture supernatant.

Preferred body fluids are selected from the group consisting of blood serum, blood plasma, seminal plasma, hydrocele fluid, spermatocele fluid, whole blood, urine, amniotic fluid, exudate, sputum, saliva and cerebrospinal fluid. In one embodiment, the body fluid is blood serum.

Tissues are preferably selected from the group consisting of native tissue, snap-frozen tissue and formalin-fixed and paraffin-embedded (FFPE) tissue.

Means and methods for the isolation (or extraction) of RNA, e.g., total RNA or miRNA, from a biological sample are known to a person skilled in the art and include commercially available kits, such as the RNeasy Mini Kit and the miRNeasy Mini Kit (both from Qiagen).

The step of converting the RNA into cDNA is preferably performed by reverse transcription (RT) using the enzyme reverse transcriptase. Means and methods for reverse transcription and synthesis of cDNA are known to the skilled person and include commercially available kits, such as the TaqMan® microRNA RT Kit (Life Technologies/Thermo Fisher Scientific).

Preferred PCR-based approaches in accordance with the present invention are quantitative real-time PCR (qRT-PCR) and digital PCR (dPCR).

In one embodiment, the qRT-PCR is fluorescence-based qRT-PCR comprising the use of a fluorescently labeled probe. In one embodiment, the fluorescently labeled probe consists of an oligonucleotide labeled with both a fluorescent reporter dye and a quencher dye (=dual-label probe). Suitable fluorescent reporter and quencher dyes/moieties are known to a person skilled in the art and include, but are not limited to the reporter dyes/moieties 6-FAM™, JOE™, Cy5® and Cy3® and the quencher dyes/moieties dabcyl, TAMRA™ and BHQ™-1, -2 or -3. Amplification of the probe-specific product causes cleavage of the probe (=amplification-mediated probe displacement), thereby generating an increase in reporter fluorescence. Other suitable fluorescent dyes for use in fluorescence-based qRT-PCR include EvaGreen® and SYBR® Green. In general, the increase of fluorescence in the reaction (measured in real time) is directly proportional to the increase of target amplificates.

dPCR is an alternate method to conventional qRT-PCR for absolute quantification and detection of nucleic acid molecules. dPCR works by partitioning a sample of DNA or cDNA into many individual, parallel PCR reactions; some of these reactions contain the target nucleic acid molecule (positive) while others do not (negative). A single molecule can be amplified a million-fold or more. During amplification, dye-labeled probes are used to detect sequence-specific targets. When no target sequence is present, no signal accumulates. Following PCR analysis, the fraction of negative reactions is used to generate an absolute count of the number of target molecules in the sample, without the need for standards or endogenous controls.

The expression "at least one miR-371a-3p-specific primer", as used herein, may, for example, refer to a single miR-371a-3p-specific primer, such as a miR-371a-3p-specific primer with a particular hairpin structure (e.g., a stem loop primer), used for conversion of RNA into cDNA, and/or to a pair of miR-371a-3p-specific primers used for qRT-PCR.

Suitable approaches for the design and preparation of miR-371a-3-specific primers and probes are known to a person skilled in the art. miR-371a-3p-specific primers and probes are also commercially available, e.g., from Life Technologies (Thermo Fisher Scientific, Carlsbad, Calif., USA) and Applied Biosystems (Darmstadt, Germany).

As used herein, the term "kit" (or "kit of parts") refers to an article of manufacture comprising one or more containers and, optionally, a data carrier. Said one or more containers may be filled with one or more of the above mentioned means or reagents. Additional containers may be included in the kit that contain, e.g., diluents, buffers and further reagents such as dNTPs. Said data carrier may be a non-electronical data carrier, e.g., a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g., an internet database, a centralized, or a decentralized database. Said data carrier may comprise instructions for the use of the kit in the methods of the invention. The data carrier may comprise a cut-off value or reference level for the expression level of miR-371a-3p. In case that the data carrier comprises an access code which allows the access to a database, said threshold value or reference level is deposited in this database. In addition, the data carrier may comprise information or instructions on how to carry out the methods of the present invention.

The term "subject", as used herein, relates to any organism such as a vertebrate, particularly any mammal, including both a human and another mammal, e.g., an animal such as a rodent, a rabbit, or a non-human primate (e.g., a monkey). The rodent may be a mouse, rat, hamster, guinea pig, or chinchilla. Preferably, the subject is a male subject. Preferably, the subject is a human. In one embodiment, a subject is a subject with or suspected of having a disease or disorder, in particular a disease or disorder as defined herein, also designated "patient" herein. In one embodiment, the subject has a family history of testicular cancer and/or has or used to have undescended testicles (cryptorchidism).

The present invention also provides a method of treating TIN in a subject or of preventing testicular cancer, more particularly testicular germ cell cancer, in a subject, the method comprising (i) detecting TIN in the subject by a method as defined herein and (ii) providing therapy to the subject. According to the present invention, therapy preferably includes radiotherapy, in particular local radiotherapy, orchiectomy and/or chemotherapy. For example, local radiotherapy may involve 16-20 Gy in fractions of 2 Gy. Radiotherapy may, for example, be performed in the case of a solitary testis. Orchiectomy may, for example, be performed if the contralateral testis is healthy. According to the present invention, therapy may be preceded by monitoring of the subject, e.g., by regular testicular ultrasound.

The present invention is further illustrated by the following examples, which are not to be construed as limiting the scope of the invention.

EXAMPLES

Comparative Example 1 a) RNA Isolation

From serum samples, total RNA was isolated using the QIAGEN miRNeasy Mini Kit according to the manufacturer's instructions with minor modifications for serum samples: for 200 µl serum, 1 ml of QIAzol and 200 µl chloroform were used.

b) cDNA Synthesis

For quantification of miR-371a-3p in serum samples, 6 µl of total RNA were reverse transcribed using the TaqMan® microRNA RT Kit (Life Technologies/Thermo Fisher Scientific) and a primer pool consisting of 1 µl each of the stem loop primers for miR-371a-3p and miR-93-5p (for normalization) (Life Technologies/Thermo Fisher Scientific, assay IDs: 002124 (miR-371a-3p) and 000432 (miR-93-5p)).

c) Preamplification

Because of the low concentration of RNA/miRNA in serum, a preamplification step was performed prior to qRT-PCR. The preamplification reaction consisted of 4 µl of the reverse transcription (RT) product, 1.12 µl assay (diluted 1:100) each of miR-371a-3p and miR-93-5p, 4 µl 5× Real Time ready cDNA Pre-Amp Master (Roche, Mannheim, Germany) and nuclease free water to add up to a total reaction volume of 20 µl. Preamplification was performed at 95° C. for 1 min, followed by 14 cycles of 95° C. for 15 s and 60° C. for 4 min. The preamplification product was then diluted 1:2 in nuclease-free water and 5 µl of the diluted preamplification product were used for qRT-PCR.

d) Detection of miRNAs by Quantitative Real-Time PCR (qRT-PCR) Using TaqMan® Probes The qRT-PCR reaction consisted of 10 µl of the FASTstart Universal Probe Master (Roche, Mannheim, Germany), 1 µl of the specific assay, and nuclease free water in a total reaction volume of 20 µl. qRT-PCR was performed on the 7500 Fast Real-Time PCR System (Life Technologies/Thermo Fisher Scientific) with the following cycling conditions: 10 min at 95° C., then 40 cycles of 15 s at 95° C. and 1 min at 60° C. Relative quantity (RQ) was calculated using the ΔΔCt method.

During the preamplification step, problems often occur, if the determination takes place at the lower detection limit of the qRT-PCR method. The miRNA molecules were pipetted into the cDNA synthesis and transcribed 1:1 into cDNA molecules. That means if there is initially only a small amount of miRNA molecules, this results only in the same small amount of cDNA, too. It is statistically impossible to pipet the same exact amount of cDNA/miRNA molecules into the reaction tube for preamplification again, if the results are to be reproduced during another experiment. The explanation for this is, that, e.g., 10 miRNA or cDNA molecules are present in in the complete reaction tube. If a certain aliquot is pipetted out of that tube into the next reaction tube for the preamplification, because of the statistical probability, it is not possible to take out the same amount of cDNA/miRNA molecules each time. Due to this it is possible that, during one pipetting step, 5 cDNA/miRNA molecules, 8 molecules, 3 molecules or even none of the molecules are transferred into the next preamplification reaction. Own experiments have shown, that this is the reason why reproducible results at the lower detection limit are very difficult or even impossible.

In Table 1, the results of the miRNA analysis of one sample are shown, which was processed after RNA isolation two times (A and B) separately by an individual cDNA synthesis, preamplification and qRT-PCR. Here, it can be clearly seen that the Ct values of the miRNA-371a-3p of the sample in the "A" run differ substantially from those obtained in the "B" run. In contrast, the Ct values of the miRNA-93 of the same sample are almost identical in each run. This results in completely different expression levels for run "A" and "B" of the target miRNA-371a-3p for the same sample. This phenomenon is due to the statistical distribution of the extremely small amount of miRNA molecules: if there are, for example, 1002 miRNA molecules compared to 1005 molecules used for the cDNA synthesis, the difference in the Ct values after preamplification and qRT-PCR is almost invisible. But if there are only 2 compared to 5 molecules pipetted into the preamplification reaction, the difference grows exponentially during the cycles (e.g., 14 cycles) of the preamplification process, and a huge difference in the expression levels respectively Ct values is detected after qRT-PCR. Assuming 100% efficiency of duplication during each cycle, after 14 cycles of preamplification 2 molecules become 16,384 molecules and 5 molecules become 6,103,515,625 molecules.

TABLE 1

Summary of experiments testing the reproducibility of measurements in the qRT-PCR (A and B are different runs of the same sample); Target Name = measured miRNA; Ct = Threshold Cycle; Ct Mean = mean value of the qRT-PCR triplicates).

| Sample Name | Target Name | Ct | Ct Mean |
|---|---|---|---|
| 8594 A | miR-371a-3p | 43.377 | 43.458 |
| 8594 A | miR-371a-3p | 43.520 | 43.458 |
| 8594 A | miR-371a-3p | 43.476 | 43.458 |
| 8594 B | miR-371a-3p | 29.493 | 29.460 |
| 8594 B | miR-371a-3p | 29.479 | 29.460 |
| 8594 B | miR-371a-3p | 29.408 | 29.460 |
| 8594 A | miR-93-5p | 12.780 | 12.791 |
| 8594 A | miR-93-5p | 12.814 | 12.791 |
| 8594 A | miR-93-5p | 12.779 | 12.791 |
| 8594 B | miR-93-5p | 12.580 | 12.631 |
| 8594 B | miR-93-5p | 12.644 | 12.631 |
| 8594 B | miR-93-5p | 12.670 | 12.631 |

These differences can also be seen in Table 2, where a cell line (HT 27), normally expressing miRNA-371a-3p at a very high level, is diluted until the lower detection limit is reached, so that the variations of the Ct values occur.

TABLE 2

Dilution series of a miRNA; Target Name = measured miRNA; Ct = Threshold Cycle; Ct Mean = mean value of the qRT-PCR duplicates; undetectable = no signal during qRT-PCR detectable).

| Sample Name | Target Name | Ct | Ct Mean | Dilution |
|---|---|---|---|---|
| 1) HT 27(1) | miR-371a-3p | 11.931 | 11.883 | 1:250 |
| 1) HT 27(1) | miR-371a-3p | 11.836 | 11.883 | |
| 1) HT 27 (2) | miR-371a-3p | 12.101 | 11.998 | |
| 1) HT 27 (2) | miR-371a-3p | 11.896 | 11.998 | |
| 1) HT 27 (3) | miR-371a-3p | 11.985 | 11.975 | |
| 1) HT 27 (3) | miR-371a-3p | 11.964 | 11.975 | |
| 2) HT 27 (1) | miR-371a-3p | 15.277 | 15.310 | 1:2500 |
| 2) HT 27 (1) | miR-371a-3p | 15.342 | 15.310 | |
| 2) HT 27 (2) | miR-371a-3p | 15.394 | 15.386 | |
| 2) HT 27 (2) | miR-371a-3p | 15.378 | 15.386 | |
| 2) HT 27 (3) | miR-371a-3p | 15.426 | 15.419 | |
| 2) HT 27 (3) | miR-371a-3p | 15.412 | 15.419 | |
| 3) HT 27 (1) | miR-371a-3p | 18.596 | 18.582 | 1:25000 |
| 3) HT 27 (1) | miR-371a-3p | 18.569 | 18.582 | |
| 3) HT 27 (2) | miR-371a-3p | 18.552 | 18.548 | |
| 3) HT 27 (2) | miR-371a-3p | 18.544 | 18.548 | |
| 3) HT 27 (3) | miR-371a-3p | 18.797 | 18.758 | |
| 3) HT 27 (3) | miR-371a-3p | 18.720 | 18.758 | |
| 4) HT 27 (1) | miR-371a-3p | 22.241 | 22.258 | 1:250000 |
| 4) HT 27 (1) | miR-371a-3p | 22.274 | 22.258 | |
| 4) HT 27 (2) | miR-371a-3p | 21.958 | 21.924 | |
| 4) HT 27 (2) | miR-371a-3p | 21.889 | 21.924 | |
| 4) HT 27 (3) | miR-371a-3p | 21.961 | 21.958 | |
| 4) HT 27 (3) | miR-371a-3p | 21.955 | 21.958 | |
| 5) HT 27 (1) | miR-371a-3p | 25.487 | 25.516 | 1:2500000 |
| 5) HT 27 (1) | miR-371a-3p | 25.546 | 25.516 | |
| 5) HT 27 (2) | miR-371a-3p | 25.355 | 25.328 | |
| 5) HT 27 (2) | miR-371a-3p | 25.301 | 25.328 | |
| 5) HT 27 (3) | miR-371a-3p | 25.064 | 25.038 | |
| 5) HT 27 (3) | miR-371a-3p | 25.013 | 25.038 | |

TABLE 2-continued

Dilution series of a miRNA; Target Name = measured miRNA; Ct = Threshold Cycle; Ct Mean = mean value of the qRT-PCR duplicates; undetectable = no signal during qRT-PCR detectable).

| Sample Name | Target Name | Ct | Ct Mean | Dilution |
|---|---|---|---|---|
| 6) HT 27 (1) | miR-371a-3p | 26.831 | 26.826 | 1:25000000 |
| 6) HT 27 (1) | miR-371a-3p | 26.820 | 26.826 | |
| 6) HT 27 (2) | miR-371a-3p | 34.186 | 34.218 | |
| 6) HT 27 (2) | miR-371a-3p | 34.251 | 34.218 | |
| 6) HT 27 (3) | miR-371a-3p | 29.800 | 29.785 | |
| 6) HT 27 (3) | miR-371a-3p | 29.769 | 29.785 | |
| 7) HT 27 (1) | miR-371a-3p | Undetectable | Undetectable | 1:250000000 |
| 7) HT 27 (2) | miR-371a-3p | Undetectable | Undetectable | |
| 7) HT 27 (2) | miR-371a-3p | Undetectable | Undetectable | |
| 7) HT 27 (3) | miR-371a-3p | Undetectable | Undetectable | |
| 7) HT 27 (3) | miR-371a-3p | Undetectable | Undetectable | |

In another experiment defined amounts of an artificial miRNA, so called cel-miRNA-39, are used exemplarily for the cDNA synthesis. The results are shown in Table 3. Once again, one can see that at about 100 miRNA molecules (approximately 0.0000000002 picomol) major differences regarding the Ct values occur.

TABLE 3 miRNA cel-miRNA-39 dilution at molecular level; Target Name = measured miRNA; Ct = Threshold Cycle; Ct Mean = mean value of the qRT-PCR duplicates; Ct MV = mean value of the three preamplification runs of the same sample; Theoretical Ct = Ct value, that was mathematically determined, based on the value of the highest concentration; ud = Undetectable, no signal during qRT-PCR detectable).

| Sample Name | Number of molecules | Number of molecules [picomol, pmol] | Concentration [M] | Target Name | Ct | Ct Mean | Ct MV | Theoretical Ct |
|---|---|---|---|---|---|---|---|---|
| 1. (1) | | | | cel-miR-39-3p | 4.067 | 4.154 | | |
| 1. (1) | | | | cel-miR-39-3p | 4.241 | 4.154 | | |
| 1. (2) | | | | cel-miR-39-3p | 4.171 | 4.214 | | |
| 1. (2) | | | | cel-miR-39-3p | 4.257 | 4.214 | | |
| 1. (3) | | | | cel-miR-39-3p | 4.334 | 4.308 | | |
| 1. (3) | $1*10^8 =$ 100000000 | 0.00016605388 | $4.15*10^{-11}$ | cel-miR-39-3p | 4.283 | 4.308 | 4.23 | 4.20 |
| 5. (1) | | | | cel-miR-39-3p | 18.928 | 18.961 | | |
| 5. (1) | | | | cel-miR-39-3p | 18.994 | 18.961 | | |
| 5. (2) | | | | cel-miR-39-3p | 19.145 | 19.145 | | |
| 5. (2) | | | | cel-miR-39-3p | 19.145 | 19.145 | | |
| 5. (3) | | | | cel-miR-39-3p | 19.318 | 19.335 | | |
| 5. (3) | $1*10^4 =$ 10000 | 0.00000001661 | $4.15*10^{-15}$ | cel-miR-39-3p | 19.351 | 19.335 | 19.15 | 17.40 |
| 6. (1) | | | | cel-miR-39-3p | 22.598 | 22.578 | | |
| 6. (1) | | | | cel-miR-39-3p | 22.557 | 22.578 | | |
| 6. (3) | | | | cel-miR-39-3p | 23.052 | 23.029 | | |
| 6. (3) | | | | cel-miR-39-3p | 23.005 | 23.029 | | |
| 6. (2) | | | | cel-miR-39-3p | 23.127 | 23.122 | | |
| 6. (2) | $1*10^3 =$ 10000 | 0.00000000166 | $4.15*10^{-16}$ | cel-miR-39-3p | 23.116 | 23.122 | 22.91 | 20.70 |
| 7. (1) | | | | cel-miR-39-3p | 24.781 | 24.822 | | |
| 7. (1) | | | | cel-miR-39-3p | 24.863 | 24.822 | | |
| 7. (2) | | | | cel-miR-39-3p | 27.048 | 27.042 | | |
| 7. (2) | | | | cel-miR-39-3p | 27.037 | 27.042 | | |
| 7. (3) | | | | cel-miR-39-3p | 26.229 | 26.234 | | |

TABLE 3-continued miRNA cel-miRNA-39 dilution at molecular level; Target Name = measured miRNA; Ct = Threshold Cycle; Ct Mean = mean value of the qRT-PCR duplicates; Ct MV = mean value of the three preamplification runs of the same sample; Theoretical Ct = Ct value, that was mathematically determined, based on the value of the highest concentration; ud = Undetectable, no signal during qRT-PCR detectable).

| Sample Name | Number of molecules | Number of molecules [picomol, pmol] | Concentration [M] | Target Name | Ct | Ct Mean | Ct MV | Theoretical Ct |
|---|---|---|---|---|---|---|---|---|
| 7. (3) | $1*10^2 = 10$ | 0.00000000017 | $4.15*10^{-17}$ | cel-miR-39-3p | 26.240 | 26.234 | 26.03 | 24.00 |
| 8. (1) | | | | cel-miR-39-3p | ud | | | |
| 8. (1) | | | | cel-miR-39-3p | ud | | | |
| 8. (2) | | | | cel-miR-39-3p | ud | | | |
| 8. (2) | | | | cel-miR-39-3p | ud | | | |
| 8. (3) | | | | cel-miR-39-3p | | | | |
| 8. (3) | 10 | 0.00000000002 | $4.15*10^{-18}$ | cel-miR-39-3p | ud | | ud | 27.30 |
| 9. (1) | | | | cel-miR-39-3p | ud | | | |
| 9. (1) | | | | cel-miR-39-3p | ud | | | |
| 9. (2) | | | | cel-miR-39-3p | ud | | | |
| 9. (2) | | | | cel-miR-39-3p | ud | | | |
| 9. (3) | | | | cel-miR-39-3p | ud | | | |
| 9. (3) | 0 | 0 | 0 | cel-miR-39-3p | ud | | ud | ud | e) Summary

The above data show that the problem of producing reliable results at the lower detection limit is related to the preamplification step. If a preamplification is performed for a sample and this preamplification product is measured using qRT-PCR, then this leads to uniform results each time (see triplicates/duplicates of the qRT-PCR assays in Table 1, Table 2, and Table 3). However, if several preamplifications are performed out of one cDNA reaction tube, and these preamplifications include different amounts of cDNA molecules according to statistics, then this leads to striking differences in the Ct values in the subsequent qRT-PCRs. Despite the best mixing procedures it is not possible to distribute the small amount of cDNA molecules from the cDNA synthesis in equal parts to the reaction tubes of the preamplification. Afterwards, the error appears and there is a high variation of the Ct values. This is explained by the doubling of the number of molecules with each of the 14 cycles.

Example 1

For the preamplification process, the sample was divided into three reaction tubes after cDNA synthesis. Afterwards, a qRT-PCR was carried out separately with each of the three reaction tubes (see Table 4 and FIG. 1). To consider the deviation of the Ct values and the resulting different expression levels (here exemplarily for miR-371a-3p), the mean value of the three RQ-values was determined mathematically (arithmetic mean) (RQ=relative quantity=expression).

TABLE 4

Results of the qRT-PCR; RQ = relative quantity; Mathematical RQ-MV Ct = mathematical mean value of RQ; Mean = mean value of the qRT-PCR triplicates; undetectable = no signal during qRT-PCR detectable.

| Sample | RQ | Mathematical RQ-MV | Ct Mean 371a-3p | Ct Mean 93 |
|---|---|---|---|---|
| 90 (1) | 0.000 | | undetectable | 11.179 |
| 90 (2) | 9.389 | 3.130 | 30.289 | 11.442 |
| 90 (3) | 0.000 | | undetectable | 11.548 |
| 71 (1) | 14.986 | | 31.809 | 13.637 |
| 71 (2) | 22.193 | 12.393 | 31.249 | 13.644 |
| 71 (3) | 0.000 | | undetectable | 13.651 |

Example 2

Figure 2:
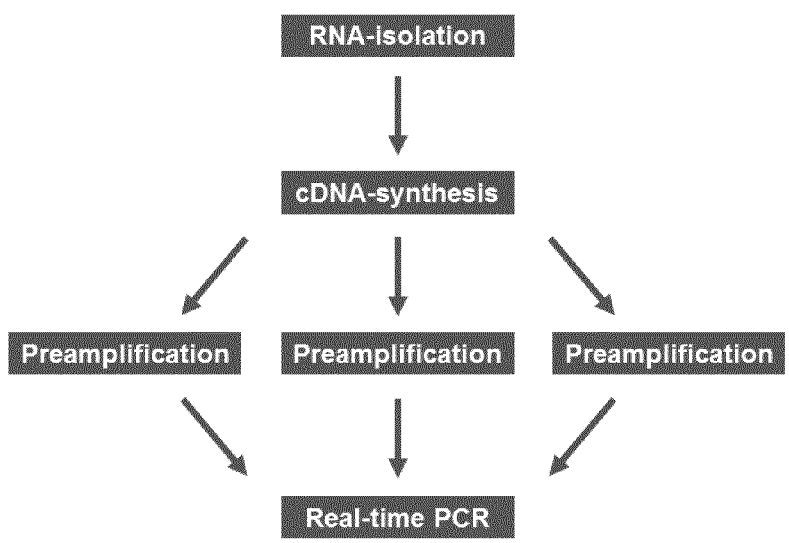
FIG. 2 shows a schematic representation of a method in accordance with the present invention (Example 2). Only one qRT-PCR is carried out with a mixture of equal amounts from three independent preamplification reactions to obtain the measured mean value for the evaluation of the data.

The sample was divided after cDNA synthesis into three reaction tubes for preamplification as in Example 1. After that, an identical volume was taken from each of the three preamplification reaction tubes and pipetted together into one reaction tube and mixed well for a single subsequent qRT-PCR (see FIG. 2).

The triplicate preamplification was made to compensate for the differences in the Ct values and determined expression levels, respectively. These differences can either be compensated by the calculation of the mean value of the RQ values (Example 1=calculated mean value/arithmetic mean) or, as in Example 2, by mixing of the three preamplification reactions and using the mix in the subsequent qRT-PCR analysis, so that a methodic mean value/measured mean for the interpretation of the results is generated. Results of this study are listed in Table 5.

TABLE 5

Results of the qRT-PCR; RQ = relative quantity;
Mathematical RQ-MV Ct = mathematical mean value of RQ;
Ct Mean = mean value of the qRT-PCR triplicates;
undetectable = no signal during qRT-PCR detectable;
Zus = sample was processed according to the protocol of
Example 2 (methodical mean value).

| Sample | RQ | Mathematical RQ MV (1), (2), (3) | Ct Mean 371a-3p | Ct Mean 93 |
|---|---|---|---|---|
| 80 (1) | 1060.735 | | 24.605 | 12.578 |
| 80 (2) | 1853.232 | | 23.906 | 12.684 |
| 80 (3) | 1365.875 | | 24.292 | 12.630 |
| 80 Zus (1, 2, 3) | 1582.389 | 1426.614 | 24.033 | 12.583 |
| 129 (1) | 154.021 | | 27.944 | 13.133 |
| 129 (2) | 244.851 | | 27.287 | 13.146 |
| 129 (3) | 420.644 | | 26.453 | 13.092 |
| 129 Zus (1, 2, 3) | 278.655 | 273.172 | 27.084 | 13.129 |
| 112 (1) | 0.000 | | | 13.204 |
| 112 (2) | 0.000 | | | 13.336 |
| 112 (3) | 0.000 | | | 13.264 |
| 112 Zus (1, 2, 3) | 0.000 | 0.000 | | 13.373 |
| 90 (1) | 0.000 | | | 11.179 |
| 90 (2) | 9.389 | | 30.289 | 11.442 |
| 90 (3) | 0.000 | | | 11.548 |
| 90 Zus (1, 2, 3) | 2.708 | 3.130 | 32.007 | 11.367 |
| 119 (1) | 79.004 | | 30.596 | 14.822 |
| 119 (2) | 5.524 | | 34.343 | 14.731 |
| 119 (3) | 0.000 | | | 14.874 |
| 119 Zus (1, 2, 3) | 31.989 | 28.176 | 31.995 | 14.917 |

Taken together, the methods exemplified in Examples 1 and 2 provide the possibility to analyze specific nucleic acid molecules even at the lower detection limit of ~0.0000000002 picomol in an exact and reliable fashion.

Example 3

The relative expression of miR-371a-3p was quantified in the blood serum of 18 patients with TIN but without testicular germ cell cancer (mean age: 33.4±6.5) and 20 controls (mean age: 37.5±10.8), using the method described in above Example 2 (see also PCT/EP2016/059604).

A. Methodology a) RNA Isolation

From serum samples, total RNA was isolated using the QIAGEN miRNeasy Mini Kit according to the manufacturer's instructions with minor modifications for serum samples: for 200 µl serum, 1 ml of QIAzol and 200 µl chloroform were used.

b) cDNA Synthesis

For quantification of miR-371a-3p in serum samples, 6 µl of total RNA were reverse transcribed using the TaqMan® microRNA RT Kit (Life Technologies/Thermo Fisher Scientific) and a primer pool consisting of 1 µl each of the stem loop primers for miR-371a-3p and miR-93-5p (for normalization) (Life Technologies/Thermo Fisher Scientific, assay IDs: 002124 (miR-371a-3p) and 000432 (miR-93-5p)).

c) Preamplification

Because of the low concentration of RNA/miRNA in serum, a preamplification step was performed prior to qRT-PCR. First the sample was divided after cDNA synthesis into three reaction tubes for preamplification. The preamplification reaction consisted of 4 µl of the reverse transcription (RT) product, 1.12 µl assay (diluted 1:100) each of miR-371a-3p and miR-93-5p, 4 µl 5× Real Time ready cDNA Pre-Amp Master (Roche, Mannheim, Germany) and nuclease free water to add up to a total reaction volume of 20 µl. Preamplification was performed at 95° C. for 1 min, followed by 14 cycles of 95° C. for 15 s and 60° C. for 4 min. After that, an identical volume was taken from each of the three preamplification reaction tubes and pipetted together into one reaction tube and mixed well for a single subsequent qRT-PCR. The preamplification product was then diluted 1:2 in nuclease-free water and 5 µl of the diluted preamplification product were used for qRT-PCR.

d) Detection of miRNAs by Quantitative Real-Time PCR (qRT-PCR) Using TaqMan® Probes The qRT-PCR reaction consisted of 10 µl of the FASTstart Universal Probe Master (Roche, Mannheim, Germany), 1 µl of the specific assay, and nuclease free water in a total reaction volume of 20 µl. qRT-PCR was performed on the 7500 Fast Real-Time PCR System (Life Technologies/Thermo Fisher Scientific) with the following cycling conditions: 10 min at 95° C., then 40 cycles of 15 s at 95° C. and 1 min at 60° C.

Relative quantity (RQ) was calculated using the ΔΔCt method.

B. Results

Figure 3:
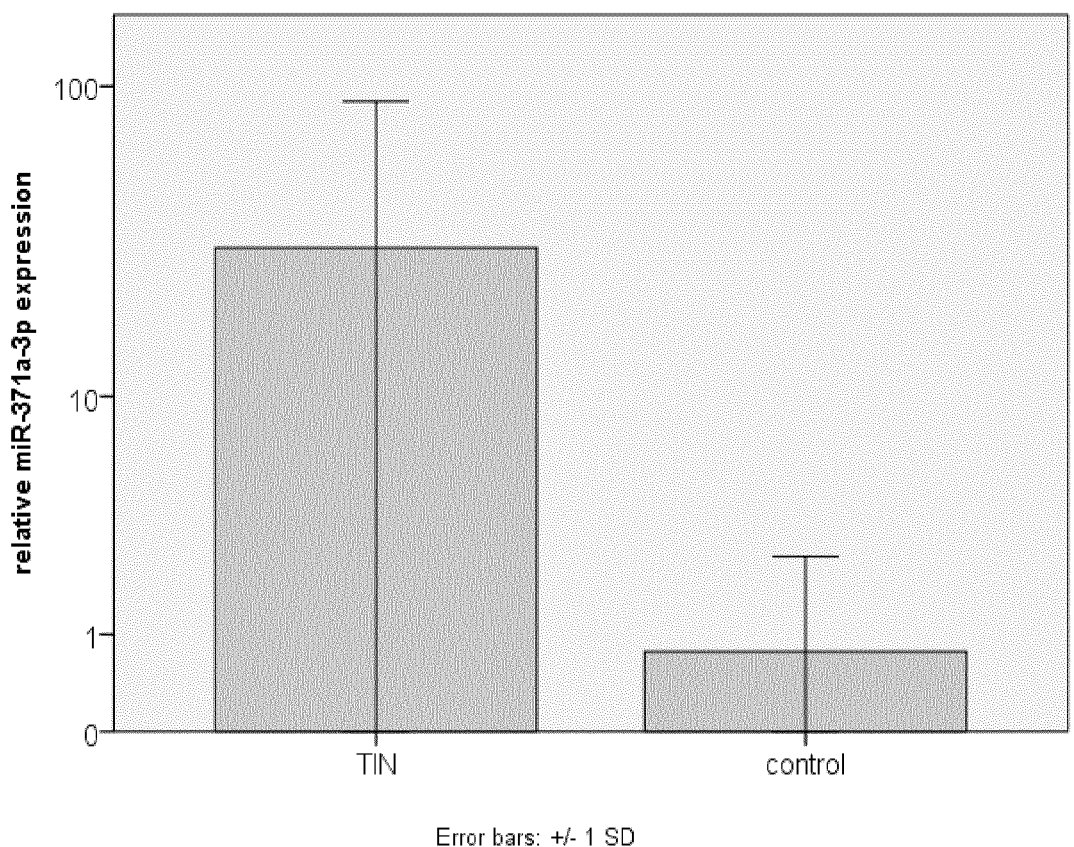
FIG. 3 shows relative miR-371a-3p expression in 18 patients with TIN and 20 controls. The error bars represent the standard deviation; the y-axis is depicted in a logarithmic scale.

Results are shown in FIG. 3. The mean miR-371a-3p expression in TIN patients was 30.75 RQ (relative quantity) with a standard deviation of 58.74. In controls, the mean expression of the miRNA was 0.77 RQ with a standard deviation of 1.73. The two-sided Mann Whitney U-test proofed this difference to be significant with $p=0.007$.

For testicular germ cell tumors, miR-371a-3p can be used as a serum-based biomarker. In a previous study, a cut-off value of RQ=5 was chosen to differentiate between tumors and controls (Dieckmann K. P. et al., 2016, Eur Urol doi:10.1016/j.eururo.2016.07.029).

Using this cut-off value, 8 of 18 (44.4%) TIN patients presented an elevated miR-371a-3p serum level, while only 1 of 20 (5%) of the controls was positive. To test if this difference in proportion was significant, a two-sided fisher exact test was employed, demonstrating a significantly different distribution with $p=0.007$. Therefore, significantly more TIN patients can be detected with the test than controls.

In the clinical routine, the classical biomarkers a-fetoprotein (AFP), the β-subunit of human chorionic gonadotropin (bHCG) and lactate dehydrogenase (LDH) are used for the diagnosis of testicular germ cell tumors. These are normally not suitable for the detection of TIN. Even when all three classical markers were combined to one panel with the assumption that one increased classical marker constituted an overall positive score, only 1 of 10 (10%) TIN patients was detectable, compared to the 8 of 18 (44.4%) TIN patients detectable with the miR-371a-3p test in accordance with the present invention.

The possibility of detecting differences between TIN patients and healthy donors opens up new opportunities for the screening and/or monitoring of, e.g., risk groups for testicular cancer. An earlier detection of TIN, which will develop in all cases into testicular germ cell tumors, can protect patients against invasive cancer diseases and, therefore, guarantee a better quality of life and cost savings for the health care system. The present invention provides the possibility for an early detection of patients with preliminary stage of germ cell tumors (TIN) in body fluids with an exact and reliable technique.

The invention claimed is:

1. A method of detecting and treating testicular intraepithelial neoplasia (TIN) in a subject, the method comprising determining the expression level of miR-371a-3p in a biological sample from the subject, wherein the expression level of miR-371a-3p is indicative of the presence or absence of TIN in the subject; wherein the subject is a human and the biological sample comprises serum, and the method further comprises the steps of:
  (i) providing a batch A comprising cDNA isolated/obtained from the biological sample, wherein step (i) comprises the steps of:
    (ia) isolating RNA from the biological sample; and
    (ib) converting the RNA isolated in step (ia) into cDNA, thereby providing batch A comprising the cDNA;
  (ii) providing three or more aliquots of batch A provided in step (i) and performing an independent polymerase chain reaction (PCR) with each of the three or more aliquots in order to amplify miR-371a-3p, thereby providing three or more batches B comprising the amplified miR-371a-3p; and
  (iii) mixing equal amounts of the three or more batches B, thereby providing a batch C, and determining the level of miR-371a-3p in batch C by a PCR-based approach;
  (iv) comparing the determined level of miR-371a-3p to a predefined cut-off threshold value;
  (v) for the determined level of miR-371a-3p that exceeds the predefined cut-off threshold value, identifying the subject as suffering from TIN; and treating the subject suffering from TIN, wherein the treating comprises radiotherapy, orchiectomy and/or chemotherapy.

2. The method of claim 1, wherein the method comprises the steps of:
  (i) providing a batch A comprising cDNA isolated/obtained from the biological sample, wherein step (i) comprises the steps of:
    (ia) isolating RNA from the biological sample; and
    (ib) converting the RNA isolated in step (ia) into cDNA, thereby providing batch A comprising the cDNA;
  (ii) providing three or more aliquots of batch A provided in step (i) and performing an independent polymerase chain reaction (PCR) with each of the three or more aliquots in order to amplify miR-371a-3p, thereby providing three or more batches B comprising the amplified miR-371a-3p; and
  (iii) determining the level of miR-371a-3p in each of the three or more batches B by a PCR-based approach and calculating the mean value of the three or more levels of miR-371a-3p determined by the PCR-based approach, wherein the mean value calculated in step (iii) corresponds to the expression level of miR-371a-3p in the biological sample.

3. The method of claim 1, wherein the predefined cut-off value corresponds to a control that is one or more reference nucleic acid molecules.

4. The method of claim 1, wherein the predefined cut-off value is an absolute expression level of miR-371a-3p.

5. The method of claim 1, wherein, in step (ii), three aliquots of batch A are provided.

6. The method of claim 1, wherein the PCR-based approach is quantitative real-time PCR (qRT-PCR) or digital PCR (dPCR).

7. The method of claim 2, wherein, in step (ii), three aliquots of batch A are provided.

8. The method of claim 2, wherein the PCR-based approach is quantitative real-time PCR (qRT-PCR) or digital PCR (dPCR).

9. The method of claim 1, wherein the serum biological sample comprises miRNA from a human with TIN.

10. The method of claim 3, wherein the one or more reference nucleic acid molecules is another miRNA.

11. The method of claim 10, wherein the another miRNA comprises miR-93-5p.

12. The method of claim 1, wherein the predefined cut-off threshold value is a relative quantity (RQ) of miR-371a-3p equal to 5.

* * * * *

SEQUENCE LISTING

<160> NUMBER OF SEQ ID NOS: 1

<210> SEQ ID NO 1
<211> LENGTH: 23
<212> TYPE: RNA
<213> ORGANISM: Homo sapiens

<400> SEQUENCE: 1
aagugccgcc aucuuuugag ugu                    23